(12) United States Patent
Gubachy et al.

(10) Patent No.: US 8,591,484 B2
(45) Date of Patent: Nov. 26, 2013

(54) LACRIMAL PUNCTUM MEASUREMENT AND OCCLUSION

(75) Inventors: James Michael Gubachy, El Paso, TX (US); Arthur Medina, Jr., San Antonio, TX (US)

(73) Assignees: AlphaMed, Inc., El Paso, TX (US); OCuSOFT, Inc., Rosenberg, TX (US)

( * ) Notice: Subject to any disclaimer, the term of this patent is extended or adjusted under 35 U.S.C. 154(b) by 55 days.

(21) Appl. No.: 13/232,633

(22) Filed: Sep. 14, 2011

(65) Prior Publication Data

US 2012/0065601 A1 Mar. 15, 2012

Related U.S. Application Data

(60) Provisional application No. 61/382,987, filed on Sep. 15, 2010.

(51) Int. Cl.
*A61F 9/00* (2006.01)
(52) U.S. Cl.
USPC .......... 604/294; 604/19; 604/27; 604/48; 604/289; 604/500
(58) Field of Classification Search
None
See application file for complete search history.

(56) References Cited

U.S. PATENT DOCUMENTS

| | | | |
|---|---|---|---|
| 4,959,048 A | 9/1990 | Seder et al. | |
| 5,178,537 A | 1/1993 | Currie | |
| 5,423,777 A | 6/1995 | Tajiri et al. | |
| 5,469,867 A | 11/1995 | Schmitt | |
| 5,741,292 A | 4/1998 | Mendius | |
| 5,826,584 A | 10/1998 | Schmitt | |
| 5,830,171 A | 11/1998 | Wallace | |
| 6,024,564 A | 2/2000 | Kesling | |
| 6,149,684 A | 11/2000 | Herrick | |
| 6,196,993 B1 | 3/2001 | Cohan et al. | |
| 6,234,175 B1 | 5/2001 | Zhou et al. | |
| 6,290,684 B1 | 9/2001 | Herrick | |
| 6,344,047 B1 * | 2/2002 | Price et al. | 606/191 |
| 6,371,122 B1 | 4/2002 | Mandelkorn | |
| 6,527,780 B1 | 3/2003 | Wallace et al. | |
| 6,629,533 B1 | 10/2003 | Webb et al. | |
| 7,404,825 B2 | 7/2008 | Herrick, II | |
| 7,607,777 B2 | 10/2009 | Zelinsky | |
| 7,998,497 B2 | 8/2011 | de Juan, Jr. et al. | |
| 2004/0068235 A1 | 4/2004 | Hallam | |
| 2004/0068286 A1 | 4/2004 | Mendius | |
| 2004/0167480 A1 * | 8/2004 | Bos | 604/289 |
| 2006/0074370 A1 | 4/2006 | Zhou | |
| 2007/0299515 A1 | 12/2007 | Herrick, II | |
| 2008/0038317 A1 | 2/2008 | Chang et al. | |
| 2008/0086101 A1 | 4/2008 | Freilich | |
| 2008/0181930 A1 | 7/2008 | Redstrom et al. | |
| 2009/0104243 A1 | 4/2009 | Utkhede et al. | |

(Continued)

OTHER PUBLICATIONS

International Search Report and Written Opinion dated Jan. 10, 2012 for co pending PCT patent application No. PCT/US2011/051690.

*Primary Examiner* — Jackie Ho
*Assistant Examiner* — Eric Bryant
(74) *Attorney, Agent, or Firm* — D'Ambrosio & Menon, PLLC; Usha Menon

(57) ABSTRACT

Methods and apparatus for treatment of dry eyes by providing a single apparatus for measuring the diameter of the lacrimal punctum and, based on the measured punctal diameter, inserting therein an appropriately sized punctum plug.

21 Claims, 4 Drawing Sheets

(56) References Cited

U.S. PATENT DOCUMENTS

| | | |
|---|---|---|
| 2009/0280158 A1 | 11/2009 | Butuner |
| 2009/0318549 A1 | 12/2009 | Butuner et al. |
| 2010/0114309 A1 | 5/2010 | de Juan, Jr. et al. |
| 2010/0209477 A1 | 8/2010 | Butuner et al. |
| 2010/0226962 A1 | 9/2010 | Redstrom et al. |
| 2010/0274224 A1 | 10/2010 | Jain et al. |
| 2011/0066067 A1 | 3/2011 | Zelinsky |
| 2011/0066138 A1 | 3/2011 | Fezza |
| 2011/0184358 A1 | 7/2011 | Weiner et al. |
| 2011/0196317 A1* | 8/2011 | Lust et al. .............. 604/290 |

* cited by examiner

LACRIMAL PUNCTUM MEASUREMENT AND OCCLUSION

PRIORITY DATA

This application claims priority to U.S. Provisional Patent Application No. 61/382,987, filed Sep. 15, 2010.

FIELD OF THE INVENTION

The invention relates generally to apparatus and methods for the treatment of dry eyes, and more specifically, to lacrimal punctum measurement and occlusion.

BACKGROUND

Dry eye syndrome affects millions of people each year, causing discomfort, redness, corneal irritation, and contact lens intolerance. Tears normally drain by passing through two lacrimal puncta (upper and lower) on the medial surface of each eyelid, then through vertical and horizontal canaliculi into the nasal cavity. Dry eye syndrome can be treated by occluding the puncta using punctal occluders, or by placing implants into the canaliculi.

SUMMARY

One or more embodiments of the invention provide apparatus and methods for the treatment of dry eyes.

One embodiment of the invention is a device for the treatment of dry eyes comprising an elongate shaft, a means for measuring a lacrimal punctum, and a means for inserting a punctal plug into the lacrimal punctum. The means for measuring a lacrimal punctum may be disposed at a first shaft end, and the means for inserting a punctal plug into the lacrimal punctum may be disposed at a second shaft end, the second shaft end longitudinally opposing the first shaft end. The first shaft end and/or the second shaft end may have a substantially conical shape. The elongate shaft may be at least partially hollow.

The means for inserting a punctal plug may have an inserter tip, the inserter tip comprising an elongate pliable rod. The inserter tip may comprise a diameter of from about 0.1 mm to about 1.0 mm. The elongate rod may have a longitudinal axis substantially coincident with the longitudinal axis of the elongate shaft. A first rod end may extend outwardly beyond the second shaft end, the first rod end capable of holding a punctal plug by press fitting the inserter tip within a recess of the punctal plug. A second rod end may be affixed to the shaft, the second rod end longitudinally opposing the first rod end.

The device may further comprise a means for ejecting a punctal plug. The means for ejecting a punctal plug may comprise an ejector button disposed proximate the second shaft end. The ejector button may be configured to apply a force to the rod to facilitate the withdrawal of the first rod end from the recess of the punctal plug.

The means for measuring a lacrimal punctum may comprise a gauge tip for measuring the diameter of a lacrimal punctum. The gauge tip may protrude outwardly from the first end and have a longitudinal axis substantially coincident with the longitudinal axis of the elongate shaft. In other embodiments, the protrusion of the gauge tip may be angled with respect to the longitudinal axis of the elongate shaft. The gauge tip may be constructed of a material selected from a group consisting of: steel, stainless steel, plastic, polycarbonate, and a combination thereof. The gauge tip may have a fixed diameter of from about 0.1 mm to about 1.0 mm. Alternatively, the gauge tip may be configured to attach a disposable tip cover having a diameter of from about 0.1 mm to about 1.0 mm. A disposable tip cover of one diameter may be interchanged with a disposable tip cover of a different diameter. The elongate shaft may further comprise a central portion disposed between the first shaft end and the second shaft end. The central portion of the elongate shaft may comprise a cross-section having a shape selected from the group consisting of: circle, ellipse, polygon, and a combination thereof.

The elongate shaft may comprise a length of from about 5 cm to about 25 cm. The shaft may be constructed of a material selected from a group consisting of: steel, stainless steel, plastic, polycarbonate, and a combination thereof. Moreover, the shaft may comprise a textured surface to facilitate a stable grip of the device.

The device may further comprise one or more distinguishing colored surfaces corresponding to a predetermined color code. The predetermined color code may correspond to the size of the corresponding punctal diameter. In one or more embodiments, the ejector button may have a different color from the shaft. Additionally, or alternatively, size information may be inscribed onto the device.

Another embodiment of the invention is a method of treating dry eyes, the method involving providing a device for the treatment of dry eyes; determining a punctal plug size to be inserted into the measured lacrimal punctum; and inserting a punctal plug into the measured lacrimal punctum.

The device for the treatment of dry eyes may comprise an elongate shaft, a means for measuring a lacrimal punctum disposed at a first shaft end, and a means for inserting a punctal plug disposed at a second shaft end, the second shaft end longitudinally opposing the first shaft end.

Determining a punctal plug size may involve inserting the means for measuring into the lacrimal punctum. The means for measuring may comprise a gauge tip for measuring the diameter of the lacrimal punctum. The gauge tip may be progressively increased or decreased in size until the gauge tip is observed to fit snugly within the lacrimal punctum. To increase or decrease the size of the gauge tip, one or more tip covers may be attached to the gauge tip to alter its diameter.

Inserting a punctal plug may involve coupling a punctal plug with the means for inserting. The coupled punctal plug may have a diameter that is substantially the same size as the diameter of the determined punctal plug size. The punctal plug may comprise a recess and the means for inserting may comprise a tip. Coupling the punctal plug with the means for inserting may involve press fitting the tip within the recess.

DETAILED DESCRIPTION

The present invention is directed at methods and apparatus for treatment of dry eyes by providing a unitary apparatus for measuring the diameter of the lacrimal punctum and, based on the measured punctal diameter, inserting therein an appropriately sized punctum plug.

One or more embodiments of the invention comprise an apparatus that combines means for measuring the diameter of the lacrimal punctum together with means for inserting an appropriately sized punctum plug into the punctum.

The apparatus may comprise a shaft, a punctum measurement end and an opposing punctum plug inserter end, the punctum measurement end and the punctum plug inserter end positioned on either ends of the shaft. Each end may be fitted with a tip. In one or more embodiments, a punctum plug ejector may be interposed on the shaft. The punctum measurement end may be configured to measure or gauge the diameter of the lacrimal punctum. A punctal diameter of 0.5 mm is common in many patients. Directly opposing the punctum measurement end may be a punctum plug inserter end for holding and inserting a punctum plug into the lacrimal punctum. The punctum plug ejector may be used to release the plug after the plug is positioned within the punctum.

Traditionally, eye-care professionals measure the diameter of the punctum using a punctal gauge, then use another separate device having an inserter to fit a punctum plug or implant into one or both puncta. The punctum may be dilated prior to inserting a plug or implant, using a dilator or sterile forceps. Dilation increases the risk of infection, rupture and irritation to surrounding tissues, and is often unnecessary.

The one or more embodiments of the invention allow an eye-care practitioner to perform the functions of measuring the size of the punctum and inserting the punctum plug utilizing a unitary or single apparatus. The device may be handheld and may be capable of being manipulated with one hand by the eye-care practitioner operating the apparatus, thereby ensuring convenience and efficiency. The utilization of a single apparatus may also result in cost-savings which may ultimately be passed down to the patients.

Figure 1:
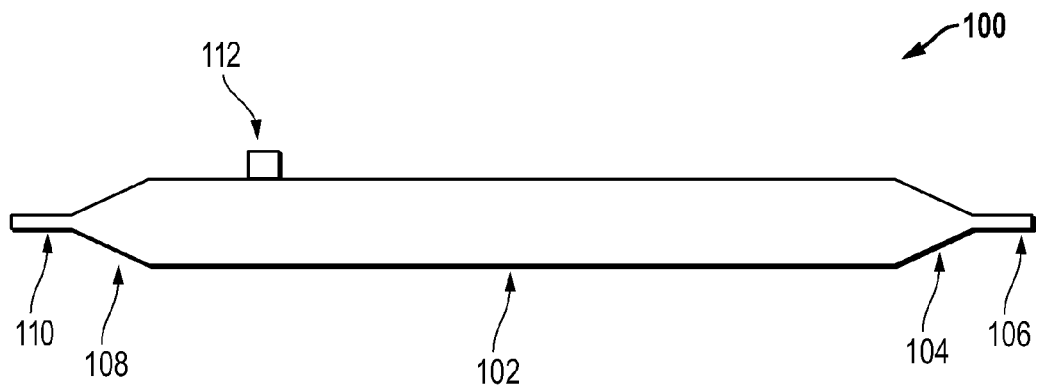
FIG. 1 shows a schematic of a side view of an apparatus in accordance with one or more embodiments of the invention.

Referring to FIG. 1, a punctum measurement and plug inserter apparatus 100 of the invention may include a shaft 102. The invention is not limited to the particular design of the apparatus shown in FIG. 1, and variations in shape and configuration are within the scope of the invention.

The apparatus 100 may be formed from stainless steel, polycarbonate, plastic, any combination of these, or other appropriate material. The shaft 102 may have raised ridges, scoring, or a roughened surface to facilitate a stable grip in the practitioner's hand. In one or more embodiments, the shaft 102 may have a hexagonal cross-section. In other embodiments, the shaft 102 may have a circular or polygonal crosssection.

The apparatus 100 may be sized or dimensioned to facilitate holding the apparatus 100 between the thumb and a forefinger of the practitioner. In one embodiment, the apparatus may be between 5 cm-25 cm in length. The shaft 102 may have a larger diameter toward its middle or may have a uniform diameter.

The apparatus 100 may narrow or taper at one end to form a punctum-measurement end 104. The punctum measurement end 104 may further comprise a gauge tip 106 for measuring the diameter of the lacrimal punctum. In some embodiments, the gauge tip 106 may be formed of steel, stainless steel, plastic, polycarbonate, or other appropriate materials. Unlike dilators disclosed in the prior art, the punctum-measurement end 104 and/or gauge tip 106 of the present apparatus 100 may be customizable, to reduce wasteful use of multiple instruments during the measuring and fitting procedure.

In some embodiments, the gauge tip 106 may have a fixed diameter in the range 0.1 mm to 1.0 mm. A practitioner may choose a fixed gauge tip 106 that approximates the punctal diameter he or she anticipates in his patient. For example, a punctal diameter of 0.5 mm is common in many patients.

Figure 2:
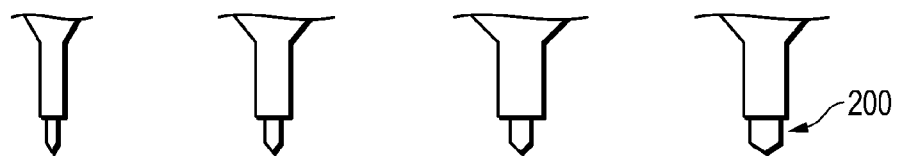
FIG. 2 shows a size comparison chart used to gauge the diameter of the lacrimal punctum in accordance with one or more embodiments of the invention.

Referring to FIG. 2, in other embodiments, the gauge tip 106 may be adapted to attach to a disposable tip cover 200 of a diameter between 0.1 mm and 1.0 mm. In these embodiments, the tip cover 200 may be used to measure the diameter of the patient's lacrimal puntum, or removed and replaced by a tip cover 200 of a different diameter, until the correct punctal diameter is determined.

One end of the apparatus 100 may narrow to form a plug inserter end 108, with an inserter tip 110 adapted to hold or attach to a punctal occluder. In some embodiments, the inserter tip 110 may be formed of stainless steel, plastic, polycarbonate, or other appropriate materials. In one or more embodiments, the punctum-measurement end 104 and/or the plug inserter end 108 may be substantially conical in shape.

In one embodiment, the inserter tip 110 may have a fixed diameter in the range of 0.1 mm to 1.0 mm. In some embodiments, a punctum plug can be fitted onto the inserter tip 110 by gently pushing the inserter tip 110 into a recessed well inside the shaft of the punctum plug. Alternatively, the punctum plug may be fitted onto the inserter tip 110 by applying gentle force with sterile forceps.

The apparatus may include an ejector 112. In one embodiment, the ejector 112 may be button or lever-shaped. In one or more embodiments, the ejector 112 may be positioned proximate the inserter end 108. The ejector 112 may be adapted to release the punctum plug from the inserter tip 110 once the practitioner has positioned the punctum plug within the lacrimal punctum.

In one embodiment of the apparatus 100, the ejector 112 may apply force to a thin metal or plastic rod or wire within the apparatus shaft 102. Pressing on the ejector 112 may pull this wire away from the punctum plug and force it off the inserter tip 110. In this way, the practitioner may release the punctum plug after it has been positioned within the patient's lacrimal punctum.

The punctum plug may be made of a material designed to safely be inserted into the patient's lacrimal puncta and canaliculi to block the flow of tears from the eye to the nasal cavity. In some embodiments, a punctum plug may be formed of plastic, silicon, extended-duration collagen, polytetrafluoroethylene (e.g. Teflon), or other medically-compatible, non-biodegradable material. In other embodiments, the punctum plug may be formed from a water-soluble, dissolvable material, such as collagen.

The apparatus 100 may be sold in separately wrapped sterile or non-sterile packets, or sold in non-sterile bulk packages. When stored as a sterile package, the apparatus may be sold as a sterile kit with two sealed trays each containing a preloaded punctal occluder, that is, a punctum plug on an inserter.

Figure 4:
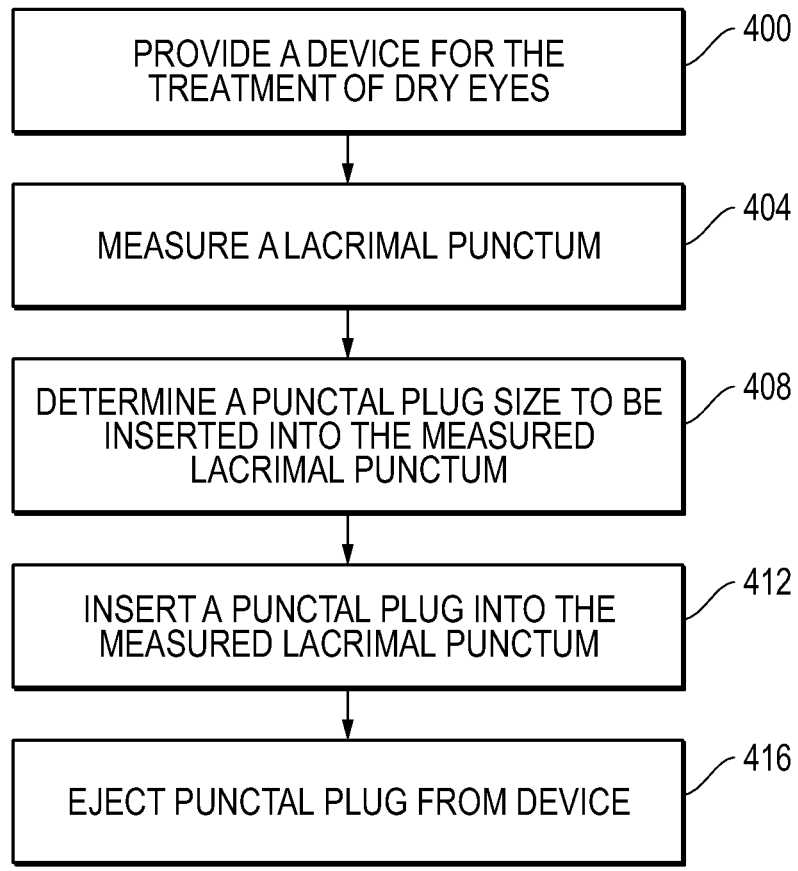
FIG. 4 shows a flow chart of a method in accordance with one or more embodiments of the invention.
Figure 5A:
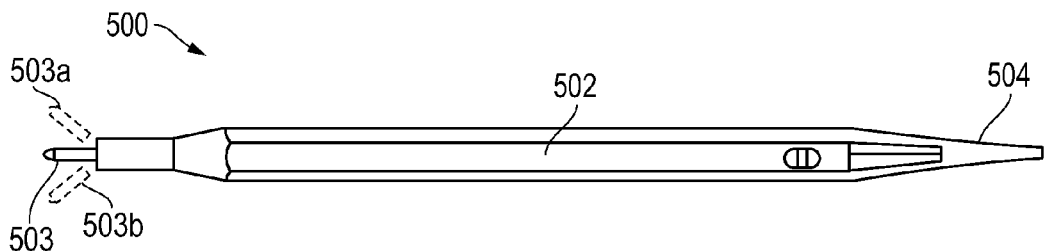
FIGS. 5A-5D show side views of an apparatus in accordance with one or more embodiments of the invention.
Figure 5B:
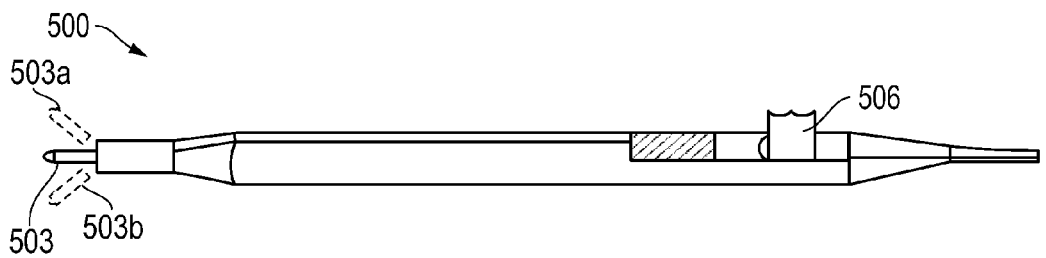
Figure 5C:
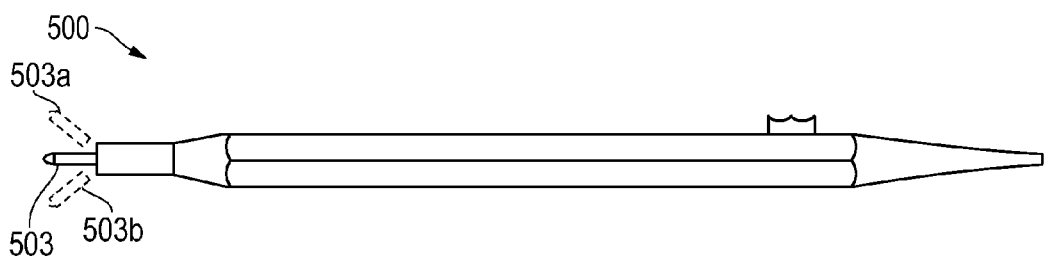
Figure 5D:
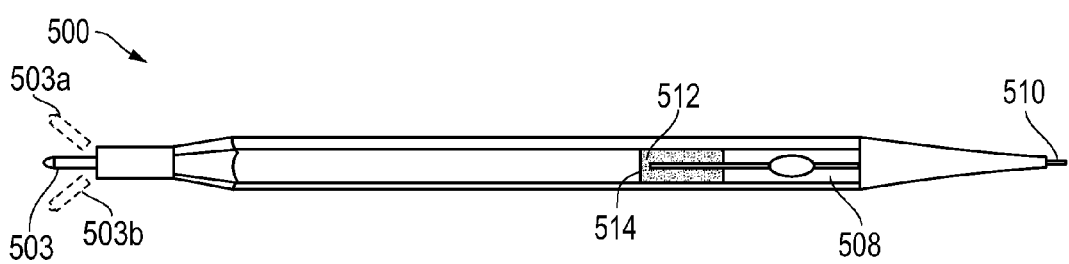

Referring to FIG. 4, in another embodiment, a method of treating dry eyes comprises, providing a device for the treatment of dry eyes 400; measuring a lacrimal punctum 404; determining a punctal plug size to be inserted into the measured lacrimal punctum 408; inserting a punctal plug into the measured lacrimal punctum 412; and ejecting the punctal plug from the device 416.

Referring to FIGS. 1 and 2, the punctum-measurement and plug-inserter apparatus 100 may be used to measure the lacrimal punctum with a gauge tip 106, 200, wherein the measurement may be repeated, with progressively increased tip diameters, until an accurate determination of the punctum diameter is reached, and dependent on the determined measurement, inserting an appropriately sized punctum plug, the punctum plug being positioned on an inserter tip 110.

Figure 3A:
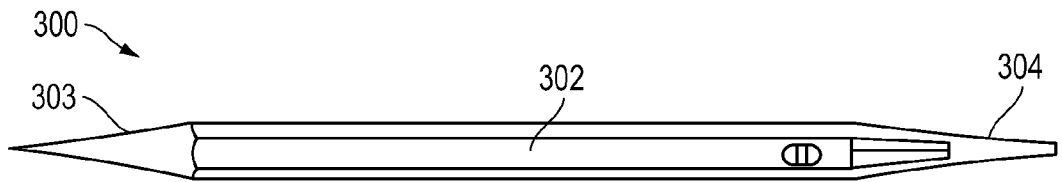
FIGS. 3A-3D show side views of an apparatus in accordance with one or more embodiments of the invention.
Figure 3B:
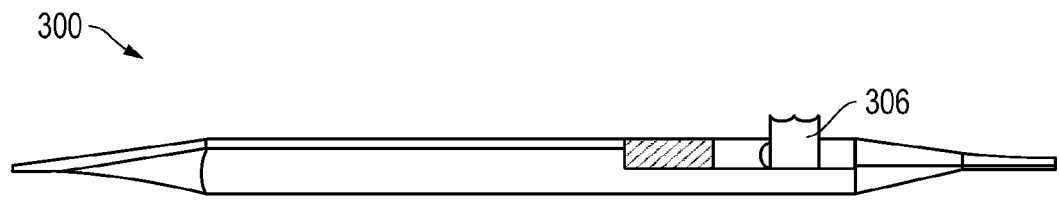
Figure 3C:
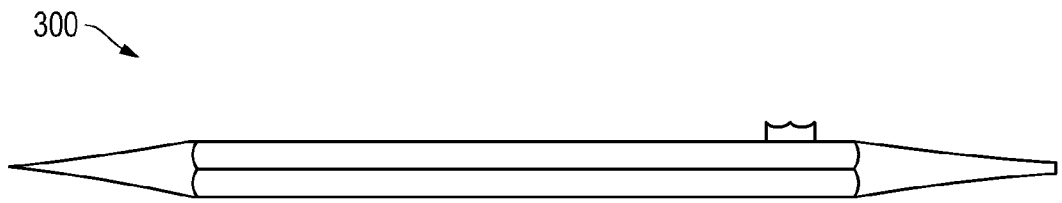
Figure 3D:
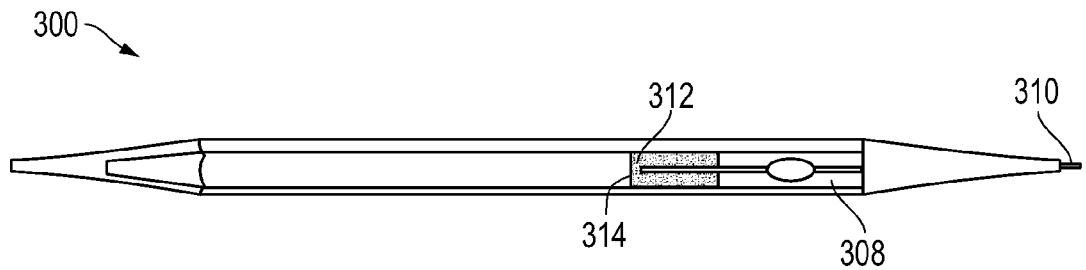

Referring to FIGS. 3A-3D, in yet another embodiment, a punctum measurement and plug inserter apparatus 300 may comprise shaft 302, the shaft 302 terminating into a conical punctum measurement end 303 (gauge tip) and a conical plug inserter end 304, the plug inserter end 304 longitudinally opposing the punctum measurement end 303. The shaft 302 may be hollowed-out. As depicted in FIG. 3C, the punctum measurement and plug inserter apparatus 300 may have a hexagonal cross-section. However, in other embodiments, the cross-section may be circular or polygonal (other than hexagonal).

The plug inserter end 304 may further comprise an inserter means 308. The inserter means 308 may comprise a metal or plastic wire or any other wiring capable of being flexed. The wire 308 may be configured to receive a punctum plug (not shown) at its tip 310. The wire 308 may be embedded within a trough 312. The trough 312 may have a backstop 314 for holding the wire 308 in place. In one or more embodiments, an adhesive may be applied to the area of contact between the wire 308 and the trough 312, the adhesive holding the wire 308 in place. When a plug ejector 306 is depressed it applies a downward force on the wire 308 proximate the backstop 314. Because one end of the wire 308 is held in place at the backstop 314, the downward force applied by the plug ejector 306 produces a tensile force on the wire 308, pulling it inwards towards the punctum measurement and plug inserter apparatus 300. A corollary is that the wire 308 shifts outwards with respect to the punctum plug. Complete depression of the plug ejector 306 may fully withdraw the tip 310 of the wire 308 from the punctum plug, thereby releasing the punctum plug into the lacrimal punctum.

In one or more embodiments, the punctum measurement and plug inserter apparatus 300 may be manufactured in multiple colors. Each color may be associated with a particular size or diameter of the punctum plug, which in turn is reflected in the diameter of the plug inserter end 304 and the punctum measurement end 303. This color-coding allows a practitioner to choose an appropriately sized punctum measurement and plug inserter apparatus 300 conveniently and quickly. In yet another embodiment, the punctum measurement and plug inserter apparatus 300 may include the diameter information for the punctum plug proximate the plug inserter end 304 and/or the punctum measurement end 303. In other embodiments, the diameter information may be coupled with a color-coded system. In one or more embodiments, the plug ejector 306 may comprise a different color from the shaft 302, the plug inserter end 304 and the punctum measurement end 303.

As illustrated in FIGS. 5A-5D, a punctum measurement and plug inserter apparatus 500 may comprise a shaft 502, the shaft 502 terminating into a punctum measurement end 503 and a plug inserter end 504. The punctum measurement end 503 may comprise a gauge tip or a protrusion that extends outwardly from the shaft 502. The punctum measurement end 503 may have a longitudinal axis substantially coincident with the longitudinal axis of the elongate shaft 502. In other embodiments, the protrusion of the punctum measure end 503a, 503b may be angled with respect to the longitudinal axis of the elongate shaft 502.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention.

We claim:

1. A handheld device for the treatment of dry eyes, the device comprising:
   an elongate shaft with a longitudinal axis;
   a means for measuring a lacrimal punctum disposed at a first shaft end, the means for measuring the lacrimal punctum in configured to receive one or more disposable tip covers; and an inserter tip, the inserter tip comprising an elongate pliable rod for inserting a punctal plug disposed at a second shaft end, the second shaft end longitudinally opposing the first shaft end, the elongate pliable rod having a longitudinal axis substantially coincident with the longitudinal axis of the elongate shaft, the elongate pliable rod comprising:
   a first rod end extending outwardly beyond the first shaft end, the first rod end capable of holding a punctal plug by press fitting the inserter tip within a recess of the punctal plug; and
   a second rod end longitudinally opposing the first rod end, the second rod end embedded within a trough in the elongate shaft, the trough having a backstop, wherein the second rod end is held in place at the backstop in the trough,
   wherein the device is devoid of a dilator.

2. The device of claim 1, further comprising a means for ejecting a punctal plug.

3. The device of claim 2, wherein the means for ejecting a punctal plug comprises an ejector button disposed proximate the second shaft end, the ejector button configured to apply a force to the rod to facilitate the withdrawal of the first rod end from the recess of the punctal plug.

4. The device of claim 1, wherein the means for measuring a lacrimal punctum comprises a gauge tip for measuring the diameter of a lacrimal punctum.

5. The device of claim 4, wherein the gauge tip is constructed of a material selected from a group consisting of: steel, stainless steel, plastic, polycarbonate, and a combination thereof.

6. The device of claim 4, wherein the gauge tip is configured to attach a disposable tip cover having a diameter of from about 0.1 mm to about 1.0 mm, wherein size information is inscribed onto the device.

7. The device of claim 1, wherein the inserter tip comprises a diameter of from about 0.1 mm to about 1.0 mm, wherein size information is inscribed onto the device.

8. The device of claim 1, wherein the elongate shaft further comprises a central portion disposed between the first shaft end and the second shaft end.

9. The device of claim 8, wherein the central portion of the elongate shaft comprises a cross-section having a shape selected from the group consisting of: circle, ellipse, polygon, and a combination thereof.

10. The device of claim 8, wherein the first shaft end and/or the second shaft end comprises a substantially conical shape.

11. The device of claim 8, wherein the elongate shaft is constructed of a material selected from a group consisting of: steel, stainless steel, plastic, polycarbonate, and a combination thereof.

12. The device of claim 8, wherein the elongate shaft further comprising a textured surface to facilitate a stable grip.

13. The device of claim 8, wherein further comprising a length of from about 5 cm to about 25 cm.

14. The device of claim 1, wherein further comprising one or more colored surfaces corresponding to a predetermined color code, the predetermined color code indicating one or more sizes corresponding to punctal diameter.

15. The device of claim 4, wherein the gauge tip comprising a protrusion extending outwardly from the first shaft end, wherein the protrusion is angled with respect to the longitudinal axis of the elongate shaft.

16. A method of treating dry eyes, the method comprising:
providing a device for the treatment of dry eyes, the device devoid of a dilator, the device comprising:
an elongate shaft;
a means for measuring a lacrimal punctum disposed at a first shaft end, the means for measuring the lacrimal ponctum is configured to receive one or more disposable tip covers; and an inserter tip, the inserter tip comprising
an elongate pliable rod for inserting a punctal plug disposed at a second shaft end, the second shaft end longitudinally opposing the first shaft end, the elongate pliable rod having a longitudinal axis substantially coincident with the longitudinal axis of the elongate shaft, the rod comprising:
a first rod end extending outwardly beyond the first shaft end, the first rod end capable of holding a punctal plug by pass fitting the inserter tip within a recess of the punctal plug; and
a second rod end longitudinally opposing the first rod end, the second rod end embedded within a trough in the shaft, the through having a backstop, wherein the second rod end is held in place at the backstop in the trough;
measuring a lacrimal punctum; determining a punctal plug size to be inserted into the measured lacrimal punctum; and inserting a punctal plug into the measured lacrimal punctum.

17. The method of claim 16, wherein determining a punctal plug size comprises inserting the means for measuring a lacrimal punctal into the lacrimal punctum, the means for measuring a lacrimal punctal comprising a gauge tip for measuring the diameter of the lacrimal punctum, the gauge tip progressively increased or decreased in size until the gauge tip is observed to fit snugly within the lacrimal punctum.

18. The method of claim 17, wherein inserting a punctal plug comprises coupling a punctal plug with the inserter tip, the coupled punctal plug having substantially the same diameter as the determined punctal plug size.

19. The method of claim 17, wherein progressively increasing or decreasing the size of the gauge tip comprises attaching one or more tip covers to alter the diameter of the gauge tip.

20. The device of claim 1, wherein the first shaft end and the second shaft end are tapered, further wherein the first shaft end is a mirror image of the second shaft end.

21. The method of claim 16, wherein the first shaft end and the second shaft end are tapered, further wherein the first shaft end is a mirror image of the second shaft end.

* * * * *